United States Patent
Einarsson

(10) Patent No.: US 10,016,219 B2
(45) Date of Patent: Jul. 10, 2018

(54) FUNCTIONAL UTERINE MANIPULATOR

(71) Applicant: THE BRIGHAM AND WOMEN'S HOSPITAL, Boston, MA (US)

(72) Inventor: Jon Einarsson, Boston, MA (US)

(73) Assignee: THE BRIGHAM AND WOMEN'S HOSPITAL, Boston, MA (US)

( * ) Notice: Subject to any disclaimer, the term of this patent is extended or adjusted under 35 U.S.C. 154(b) by 393 days.

(21) Appl. No.: 14/375,200

(22) PCT Filed: Nov. 16, 2012

(86) PCT No.: PCT/US2012/065584
§ 371 (c)(1),
(2) Date: Jul. 29, 2014

(87) PCT Pub. No.: WO2013/115892
PCT Pub. Date: Aug. 8, 2013

(65) Prior Publication Data
US 2015/0005780 A1    Jan. 1, 2015

Related U.S. Application Data

(60) Provisional application No. 61/592,125, filed on Jan. 30, 2012.

(51) Int. Cl.
*A61B 17/42*    (2006.01)
*A61B 17/32*    (2006.01)
(Continued)

(52) U.S. Cl.
CPC .. *A61B 17/4241* (2013.01); *A61B 17/320016* (2013.01); *A61B 2017/00557* (2013.01);
(Continued)

(58) Field of Classification Search
CPC ............... A61B 17/42; A61B 17/4241; A61B 2017/4216; A61B 2017/4225;
(Continued)

(56) References Cited

U.S. PATENT DOCUMENTS 5,275,608 A * 1/1994 Forman ................. A61B 17/29
606/170
5,314,445 A * 5/1994 Heidmueller .. A61B 17/320016
606/174
(Continued)

FOREIGN PATENT DOCUMENTS

EP    0229620 A2    7/1987
RU    2036669 C1    6/1995
(Continued)

OTHER PUBLICATIONS

PCT International Search Report and Written Opinion, PCT/US2012/065584, dated Feb. 14, 2013, 10 pages.

*Primary Examiner* — Ryan J Severson
*Assistant Examiner* — Charles Wei

(57) ABSTRACT

A uterine manipulator operable to detach the uterus and cervix from the vagina. The uterine manipulator includes an umbrella-like tip that creates a secure connection between the uterine manipulator and the uterus and cervix. The uterine manipulator also includes a pneumooccluder that enables rotation of the manipulator shaft while maintaining pneumoperitoneum. The uterine manipulator further includes a cutter that travels in a circle at the junction of the cervix and the vagina, permitting detachment of the uterus and cervix from the top of the vagina.

15 Claims, 12 Drawing Sheets

(51) Int. Cl.
*A61B 17/00* (2006.01)
*A61B 17/29* (2006.01)

(52) U.S. Cl.
CPC . *A61B 2017/291* (2013.01); *A61B 2017/2905* (2013.01); *A61B 2017/4225* (2013.01)

(58) Field of Classification Search
CPC .... A61B 2017/2929; A61B 2017/2923; A61B 2017/2946; A61B 2017/291; A61B 17/12027–17/12045; A61B 17/4208; A61B 2017/4233
USPC .......................... 606/119, 191, 198, 205–211
See application file for complete search history.

(56) References Cited

U.S. PATENT DOCUMENTS

| | | | | |
|---|---|---|---|---|
| 5,409,496 A | * | 4/1995 | Rowden | A61B 17/4241 606/119 |
| 5,520,698 A | * | 5/1996 | Koh | A61B 17/4241 128/898 |
| 5,540,700 A | * | 7/1996 | Rowden | A61B 17/4241 600/201 |
| 5,643,285 A | * | 7/1997 | Rowden | A61B 17/4241 606/119 |
| 5,840,077 A | * | 11/1998 | Rowden | A61B 17/4241 606/119 |
| 6,030,406 A | * | 2/2000 | Davis | A61B 17/00008 604/104 |
| 6,156,006 A | * | 12/2000 | Brosens | A61B 17/00234 604/104 |
| 8,079,963 B2 | * | 12/2011 | Rosenblatt | A61B 5/053 600/202 |
| 8,323,278 B2 | * | 12/2012 | Brecheen | A61B 17/42 606/170 |
| 8,608,738 B2 | * | 12/2013 | Brecheen | A61B 17/42 606/170 |
| 8,858,586 B2 | * | 10/2014 | Chang | A61B 17/24 606/196 |
| 2001/0021854 A1 | * | 9/2001 | Donnez | A61B 17/4241 606/119 |
| 2008/0147113 A1 | * | 6/2008 | Nobis | A61B 17/29 606/205 |
| 2014/0180282 A1 | * | 6/2014 | Brecheen | A61B 17/42 606/45 |
| 2015/0250992 A1 | * | 9/2015 | Morriss | A61M 29/02 606/198 |

FOREIGN PATENT DOCUMENTS

SU 731961 A1 5/1980
WO 9611641 A1 4/1996

* cited by examiner

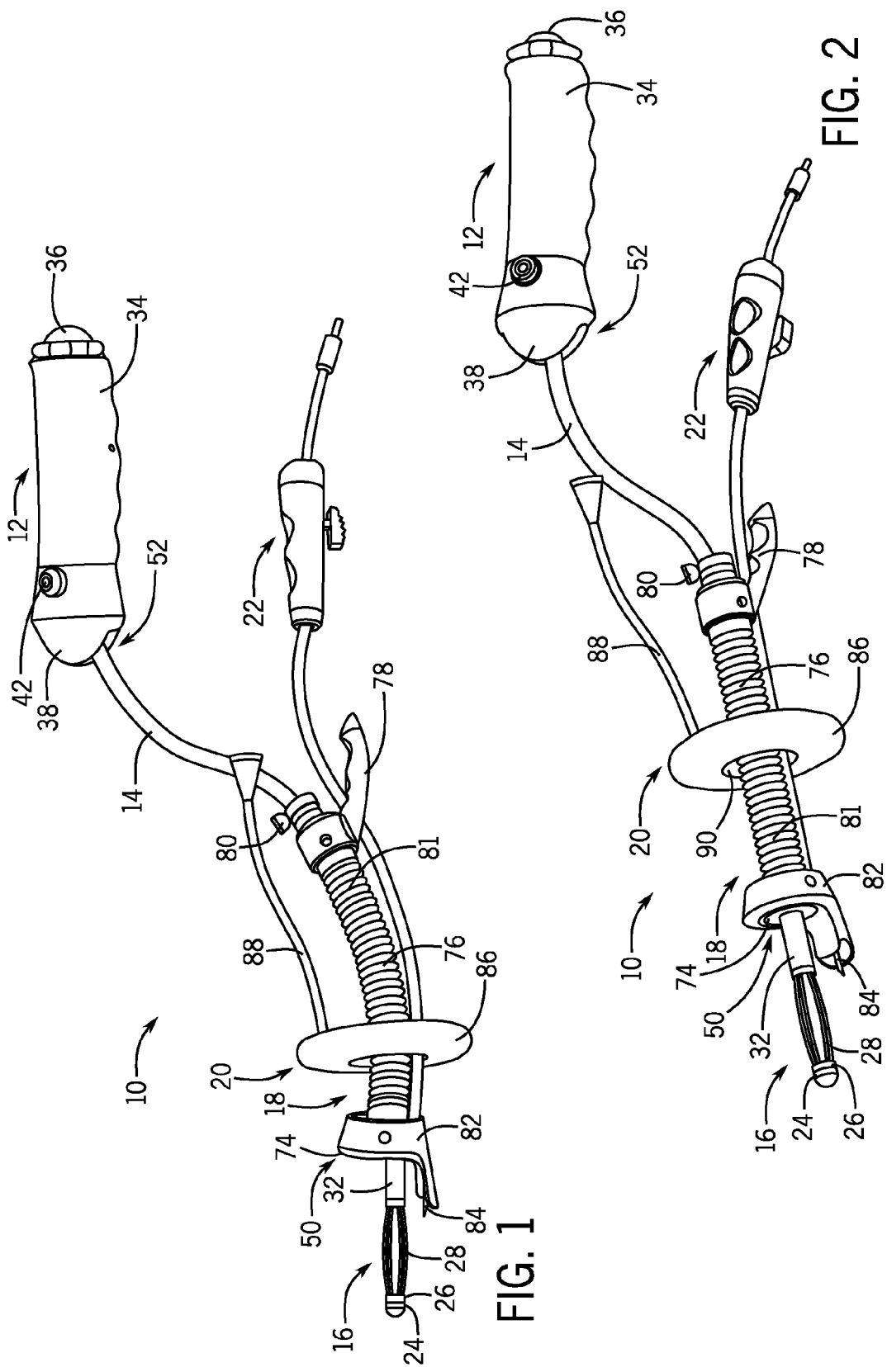

FUNCTIONAL UTERINE MANIPULATOR

CROSS-REFERENCE TO RELATED APPLICATIONS

This application represents the national stage entry of PCT International Application No. PCT/US2012/065584 filed Nov. 16, 2012, which claims the benefit of U.S. Provisional Patent Application Ser. No. 61/592,125 filed Jan. 30, 2012, the disclosures of which are hereby incorporated by reference in their entirety for all purposes.

BACKGROUND OF THE INVENTION

The present invention relates generally to uterine manipulators and methods of using a uterine manipulator for detaching the uterus and cervix from the vagina.

Uterine manipulators are conventionally used as aids in laparoscopic hysterectomies to mobilize and position the uterus, to provide better visualization of the vagina and the cervix for facilitating their separation, and to remove the uterus after colpotomy is performed. Basic uterine manipulators include a handle, a shaft, an inflatable balloon, and a cervical stop. The handle is located at one side of the shaft and the inflatable balloon is located near the tip of the other side of the shaft. The inflatable balloon is maneuvered into the uterus in a deflated condition and then inflated (e.g., via saline or water injected through the shaft) to help stabilize the uterine manipulator during the procedure and also to help remove the uterus after it has been separated from the vagina. Once the uterine manipulator is positioned, the cervical stop can be adjusted to abut the cervix.

More complex uterine manipulators include a handle, a shaft, an inflatable balloon, a cervical cup, and an occluder. The handle, the shaft, and the inflatable balloon can have similar functions as described above. The cervical cup can be fitted around the cervix and pressed inward against the vaginal fornix in order to provide an observable or palpable landmark of the incision point for dissecting the cervix and uterus from the vagina and to physically separate the incision area from the nearby ureters. Using such complex uterine manipulators, the incision for detaching the uterus and cervix from the vagina is executed laparoscopically (e.g., via a hook electrode). The occluder, positioned within the vagina when the uterine manipulator is set, makes continuous radial contact with the vaginal wall in order to maintain pneumoperitoneum after the incision between the vagina and the cervix has been made. The occluder may be a silicone cup pushed up the shaft and pressed into the vagina, or a balloon slid onto the shaft and inflated so that it presses against the vaginal wall.

Current uterine manipulators can present drawbacks in certain situations. For example, cup or balloon type occluders are in direct contact with the shaft and slid along the shaft for placement within the vagina. In some cases, this can inhibit rotation of the shaft when attempting to manipulate the position of the uterus, for example to make incisions around the fornix. In other cases, attempting to rotate the shaft can cause the occluder to slide along the shaft and disengage from the vaginal wall, resulting in a loss of pneumoperitoneum. In addition, current uterine manipulators only serve to provide guidance for detaching the uterus and the cervix from the vagina via laparoscopic tools.

Therefore, it would be desirable to have a uterine manipulator that overcomes these drawbacks.

SUMMARY OF THE INVENTION

The present invention provides a uterine manipulator that is operable to detach the uterus and cervix from the vagina. The uterine manipulator includes an umbrella-like tip that creates a secure connection between the uterine manipulator and the uterus and cervix. The uterine manipulator also includes a pneumooccluder that enables rotation of the manipulator shaft while maintaining pneumoperitoneum. The uterine manipulator further includes a cutter that travels in a circle at the junction of the cervix and the vagina, permitting detachment of the uterus and cervix from the top of the vagina.

In accordance with one aspect of the invention, the uterine manipulator includes a shaft with a first end and a second end, a handle coupled to the first end, and a tip assembly coupled to the second end and adapted for insertion into the uterus. The tip assembly includes a tip housing, a tip shaft retractable within the tip housing, and expansion elements positioned over the tip shaft and abutting an edge of the tip housing. The tip assembly is capable of being situated into an expanded position where the tip shaft is retracted into the tip housing, causing the expansion elements to expand outward in their circumferential direction, and a retracted position where the tip shaft is retracted out from the tip housing, causing the expansion elements to retract inward in their circumferential direction.

In accordance with another aspect of the invention, the uterine manipulator includes a cutter assembly coupled around the shaft and adapted to receive the cervix when the tip assembly is inserted into the uterus. The cutter assembly includes a tube, and a backstop and a cutting handle coupled to the tube. The backstop includes a cup portion and a cutter. The cup portion is adapted to force the vaginal fornix away from the ureters when the uterine manipulator is inserted into the uterus. The cutter is capable of piercing tissue along the vaginal fornix, and the backstop is capable of being rotated to allow the cutter to completely detach the cervix from the vagina.

In accordance with yet another aspect of the invention, the uterine manipulator includes a pneumooccluder coupled around the shaft and capable of being positioned within the vaginal cavity when the tip assembly is inserted into the uterus. The pneumooccluder includes a bearing positioned around the shaft, a balloon positioned around the bearing, and an occluder tube coupled to the balloon. The bearing allows the shaft to be rotated independently from the balloon.

The foregoing and other advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIG. 1 is a perspective view of a Uterine manipulator according to the present invention.

FIG. 2 is another perspective view of the uterine manipulator of FIG. 1.

DETAILED DESCRIPTION OF THE INVENTION

Figure 12A:
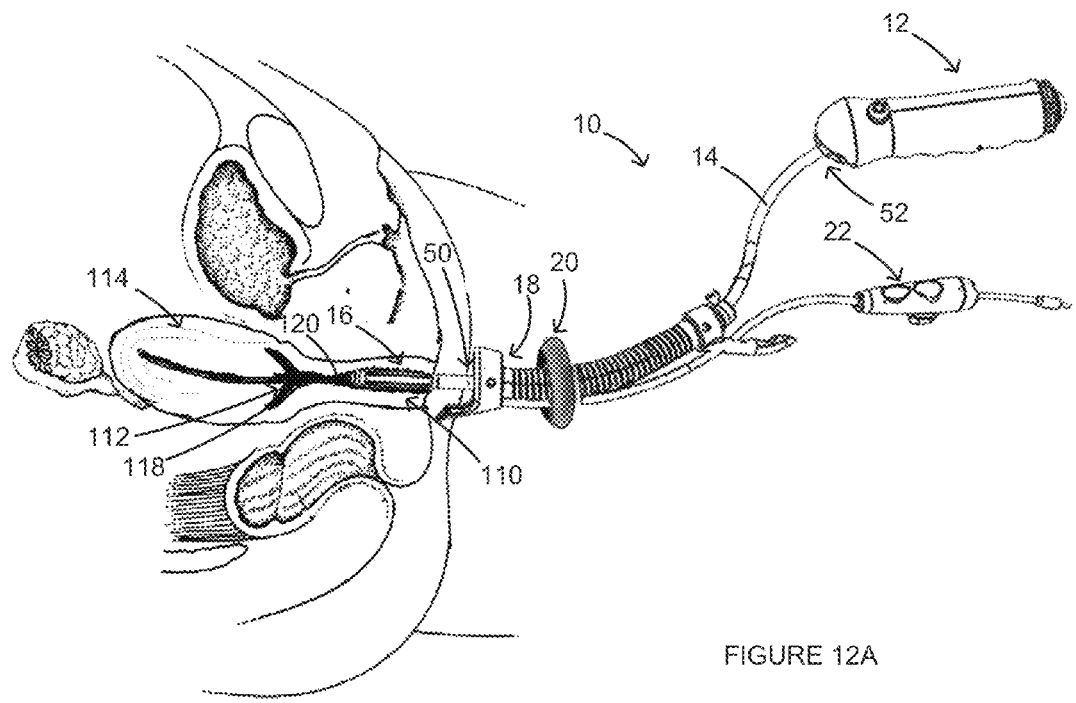
FIGS. 12A-12D are cross-sectional views of a pelvic cavity and the uterine manipulator of FIG. 1.
Figure 12B:
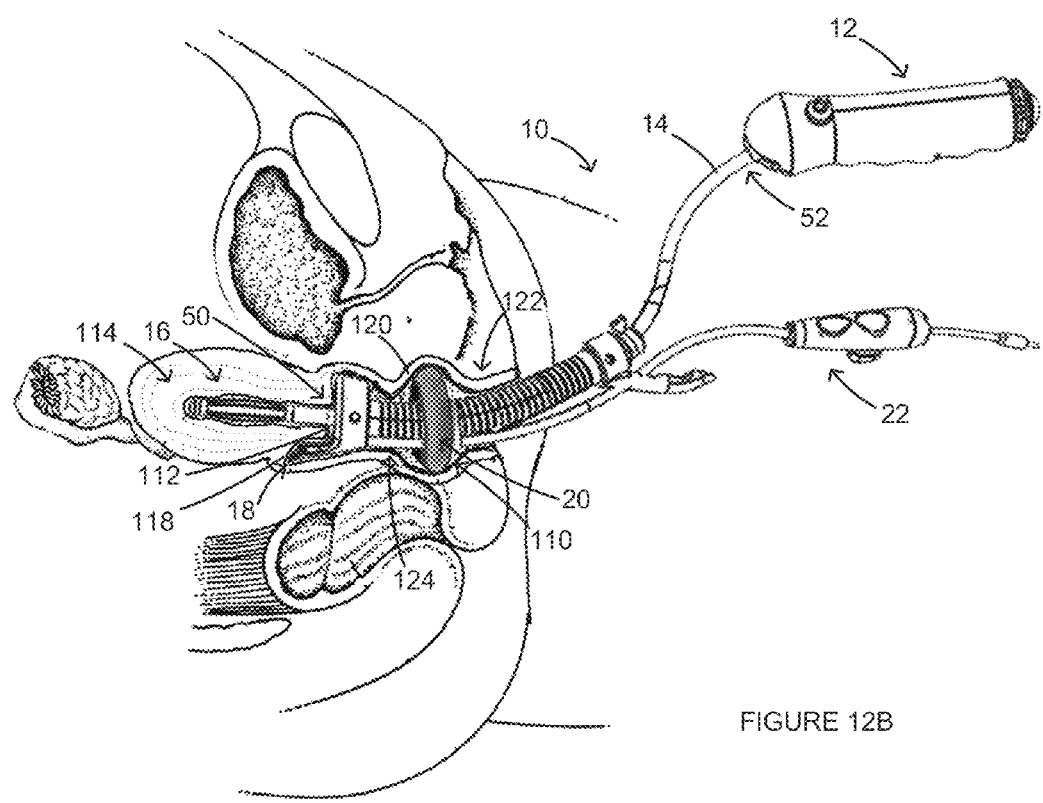
Figure 12C:
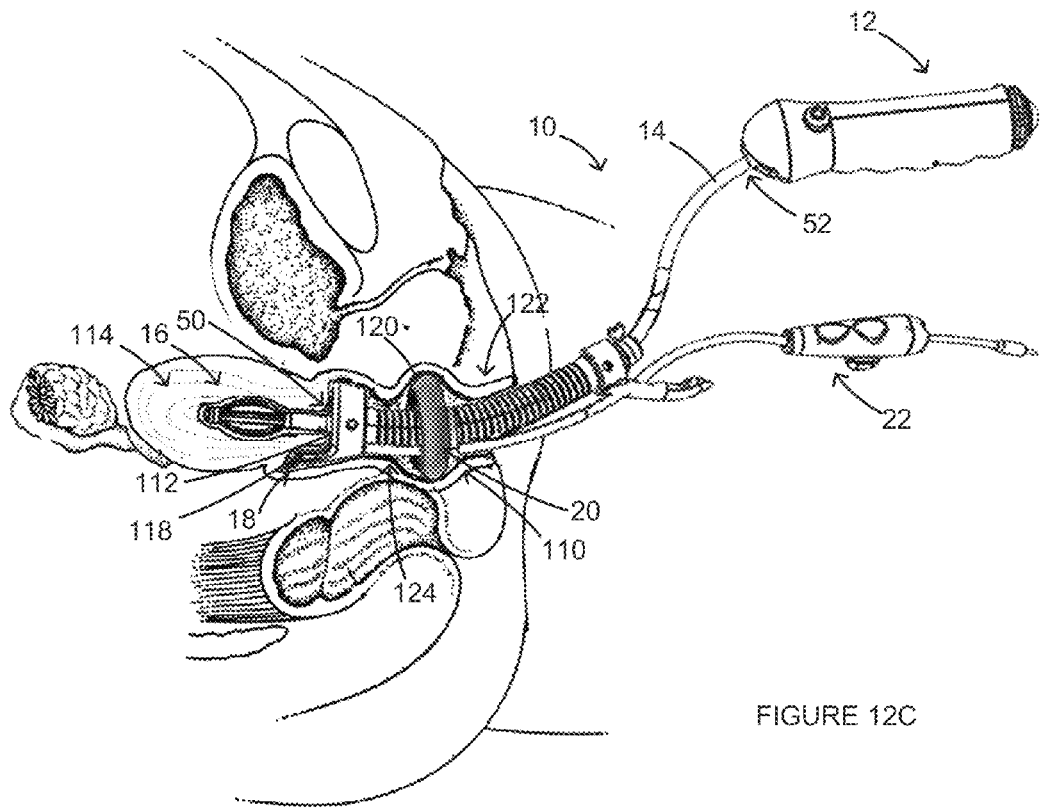

FIGS. 1 and 2 illustrate a functional uterine manipulator 10, according to the invention, for use in vaginal hysterectomies, laparoscopically assisted vaginal hysterectomies, and/or other pelvic procedures. The uterine manipulator 10 can include a handle 12, a shaft 14, a tip assembly 16, a cutting assembly 18, a pneumooccluder 20, and an electrical connector assembly 22. During use, the uterine manipulator 10 can be inserted into a patient's vagina 110, as shown in FIG. 12A, and then guided past the cervix 112 and into the uterus 114, as shown in FIG. 12B, using the handle 12. More specifically, as shown in FIGS. 12B and 12C, when the uterine manipulator 10 is inserted, the tip assembly 16 can be positioned in the uterus 114, the cutting assembly 18 can be positioned adjacent to the vaginal fornix 118 and can press against the cervix 112, and the pneumooccluder 20 can be positioned inside the vagina 110.

Figure 3:
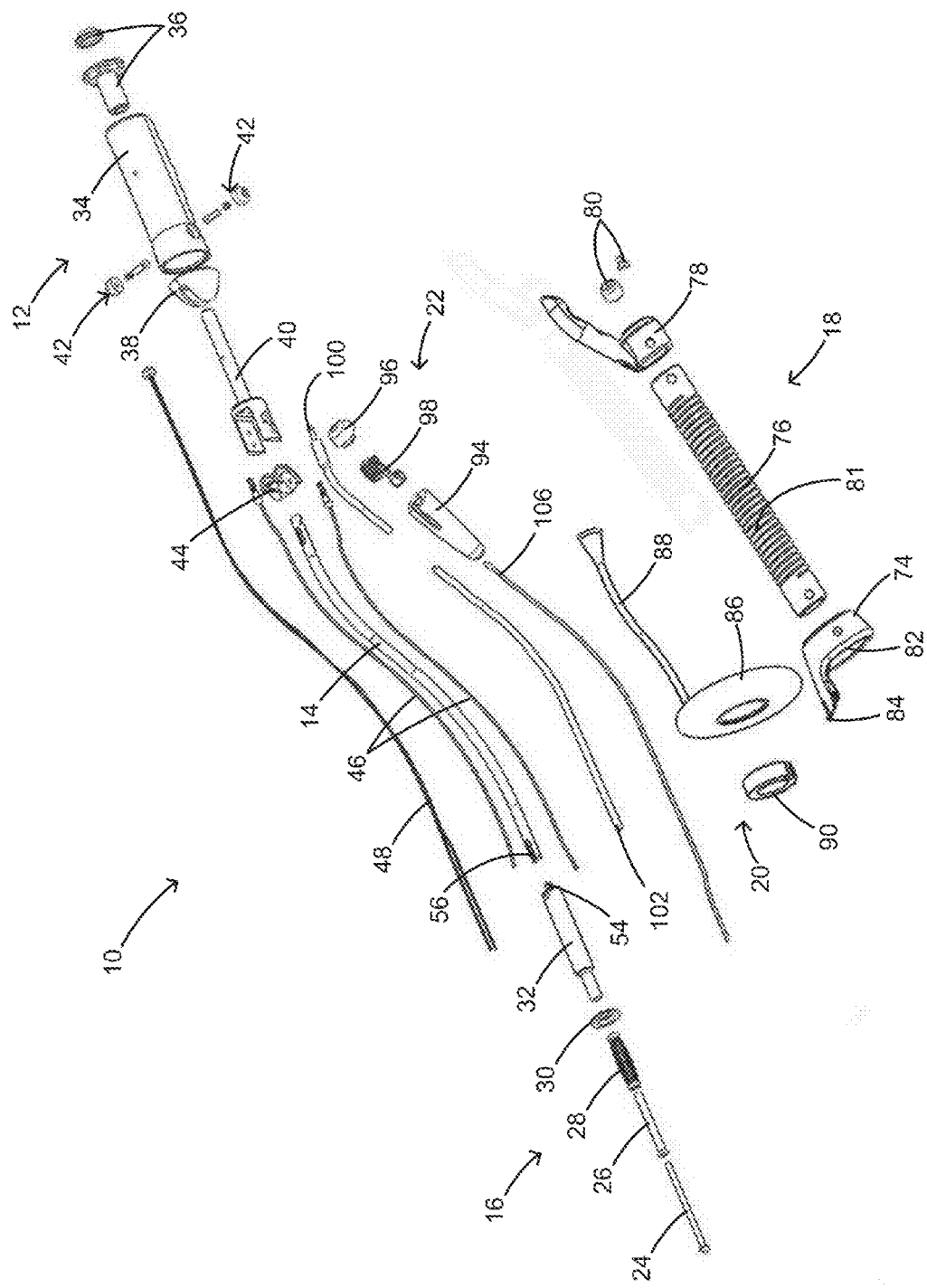
FIG. 3 is an exploded perspective view of the uterine manipulator of FIG. 1.
Figure 4A:
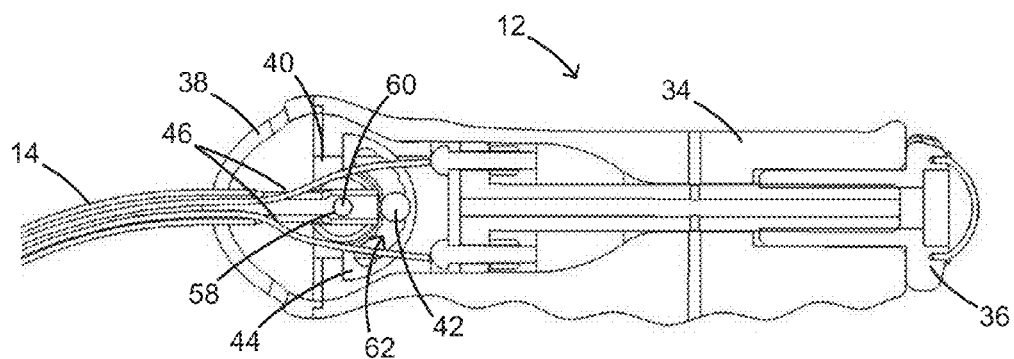
FIGS. 4A and 4B are partial side views of a handle and a tip assembly, respectively, of the uterine manipulator of FIG. 1.
Figure 4B:
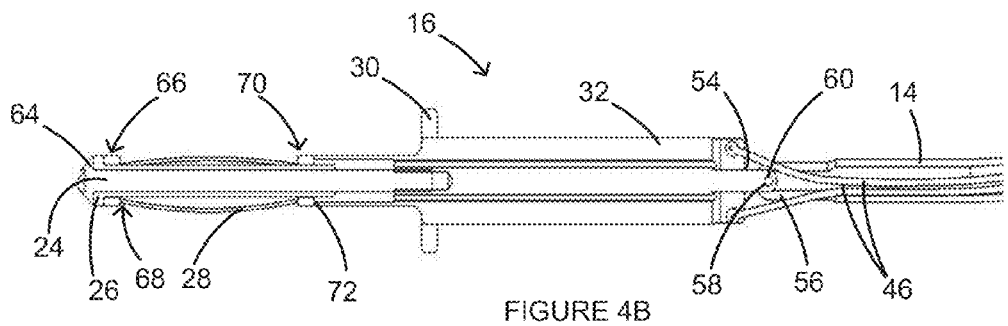
Figure 5A:
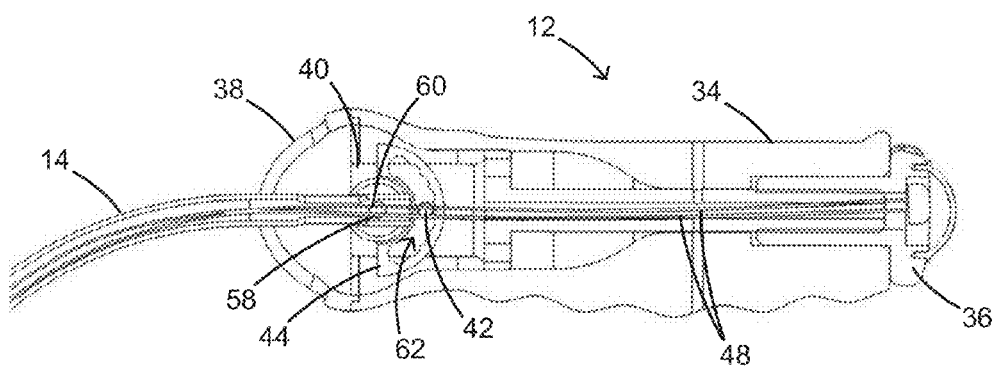
FIGS. 5A and 5B are additional partial side views of the handle and the tip assembly, respectively, of the uterine manipulator of FIG. 1.
Figure 5B:
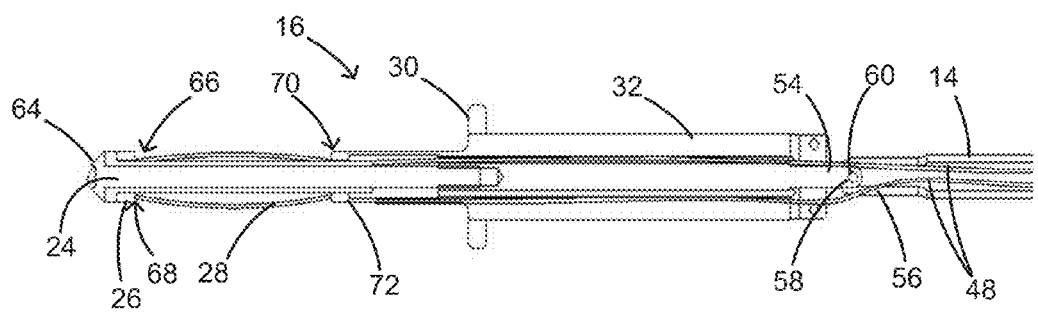

As shown in FIG. 3, the tip assembly 16 can include an expansion tip 24, a tip shaft 26, expansion elements 28, an abutment 30, and a tip housing 32, and the handle 12 can include a handle housing 34, an expansion actuator 36, a cap 38, a hinge 40, hinge pins 42, and a pivoting element 44. The shaft 14 can be coupled to the tip assembly 16 via the tip housing 32, and can be coupled to the handle 12 via the pivoting element 44. The tip assembly 16 can also be coupled to the handle 12 via connectors 46. As shown in FIGS. 4A and 4B, the connectors 46 can be routed from inside the handle housing 34, through the shaft 14, and coupled to the tip housing 32. In addition, as shown in FIGS. 3, 5A and 5B, expansion connectors can be coupled to the expansion actuator 36, routed from inside the handle housing 34 through the shaft 14 and coupled to the expansion tip 24 for actuating the tip assembly 16, as further described below. In some implementations of the present invention, some or all of the components of the uterine manipulator 10 can be disposable. In addition, in some implementations, some or all of the components may be removable from one another, for example, so that disposable components can be uncoupled from permanent components and replaced with new disposable components.

Figure 6A:
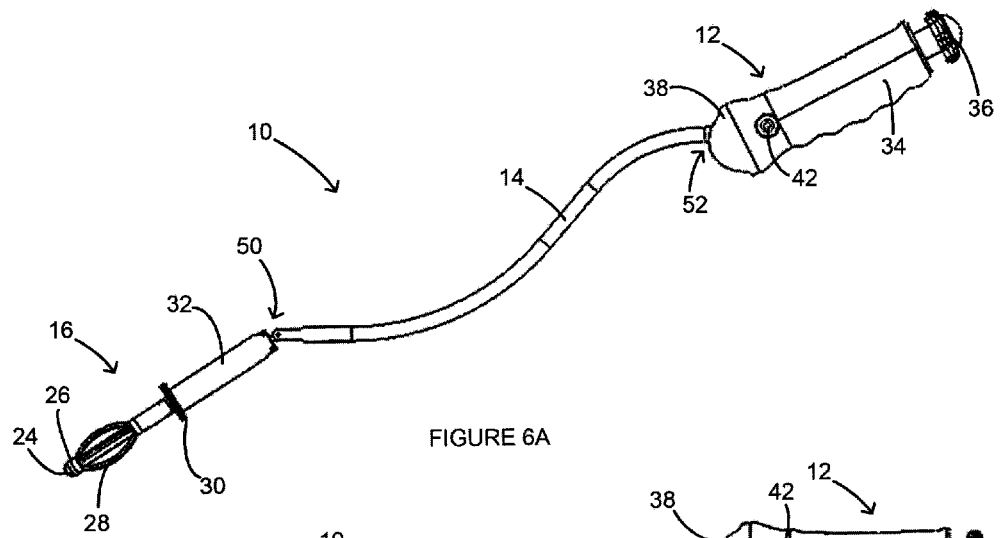
FIGS. 6A-6C are side views of the uterine manipulator of FIG. 1 in different pivoting positions.
Figure 6B:
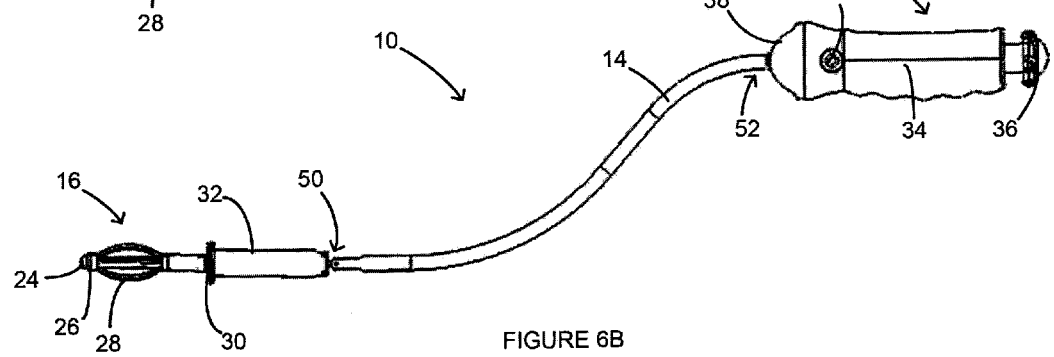
Figure 6C:
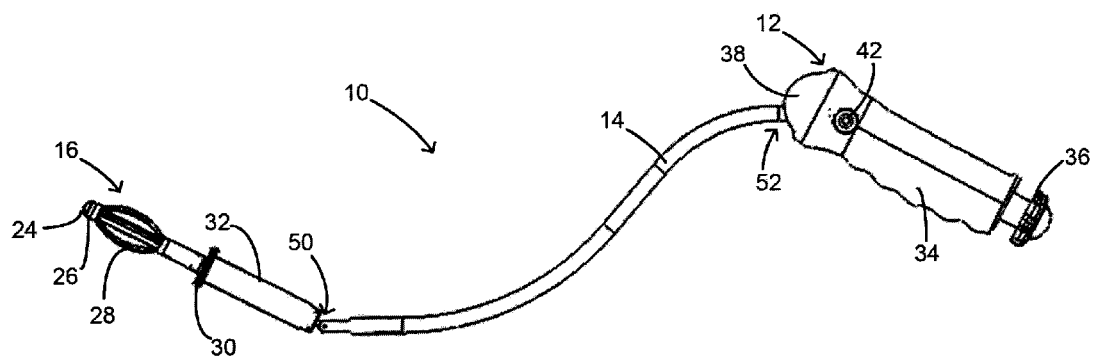
Figure 7A:
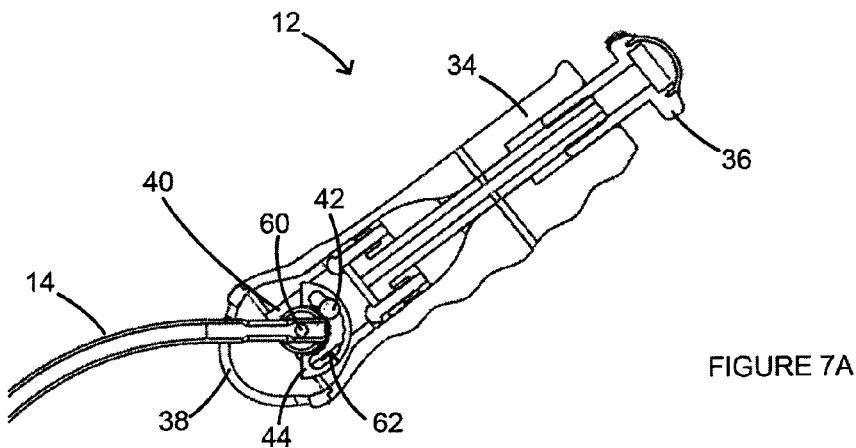
FIGS. 7A-7D are side and front views of the handle assembly of the uterine manipulator of FIG. 1 in different pivoting positions.
Figure 7B:
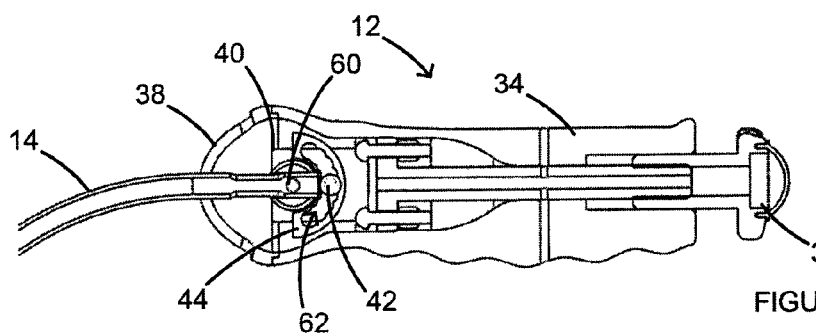
Figure 7C:
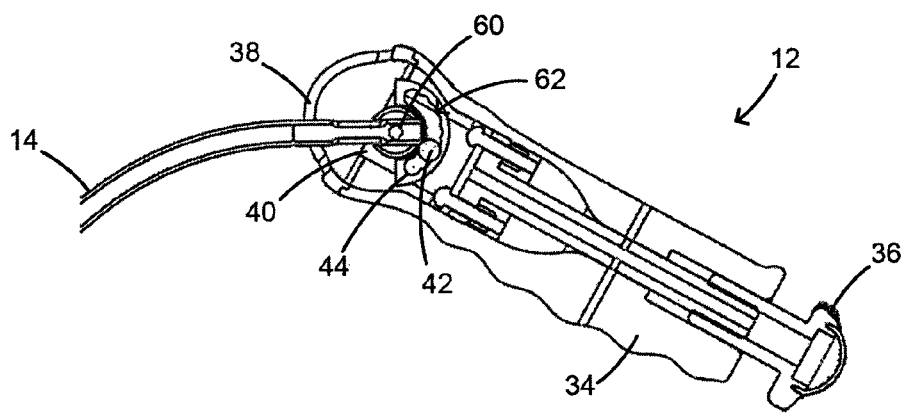
Figure 7D:
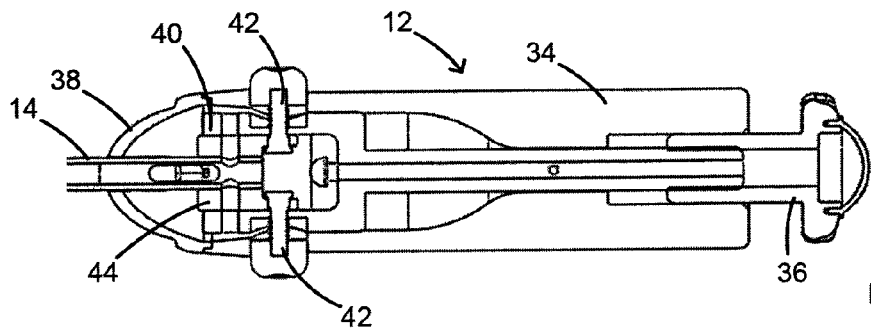

As shown in FIGS. 6A-6C, the tip assembly 16, the shaft 14, and the handle 12 can be pivotable relative to each other at two separate pivot points 50, 52. The first pivot point 50 and the second pivot point 52 can facilitate insertion of the uterine manipulator 10 into the uterus 114 and can also facilitate repositioning of the uterus 114 during the hysterectomy. The first pivot point 50 can be located at the connection between the tip housing 32 and the shaft 14. For example, as shown in FIGS. 4B and 5B, the end 54 of the tip housing 32 can be positioned between end components 56 of the shaft 14 so that through holes 58 in each component 54, 56 are aligned, and a pin 60 can be routed through the through holes 58 to permit a pivotable connection. The second pivot point 52 can be located at the connection between the shaft 14 and the handle 12. For example, as shown in FIGS. 4A, 5A, and 7A-7D, the shaft 14 can be fixed to the pivoting element 44 (e.g., via a pin 60 and through hole 58 connection) and the pivoting element 44 can be pivotable about the hinge 40 within the handle housing 34. More specifically, the hinge pins 42 can extend through the handle housing 34, the hinge 40, and a track 62 of the pivoting element 44, as best shown in FIG. 7D. The track 62 can be ribbed so that the hinge pins 42 cannot freely slide within it. Rather, the hinge pins 42 can be substantially fixed at specific points along the ribbed track 62 and only adjusted by applying an amount of force. This can prevent unwanted movement of the second pivot point 52 unless a deliberate force is applied.

In some implementations of the present invention, an additional mechanism (for example, in the handle 12), can be used to control both pivot points 50, 52. For example, if the additional mechanism is actuated in a first direction, both pivot points 50, 52 can be locked in place. If the additional mechanism is actuated in a second direction, both pivot points 50, 52 can be unlocked and maneuverable. In addition, in some implementations of the invention, the shaft 14 can be constructed of a non-rigid, flexible material to facilitate insertion of the uterine manipulator 10 into the uterus 114.

Figure 8A:
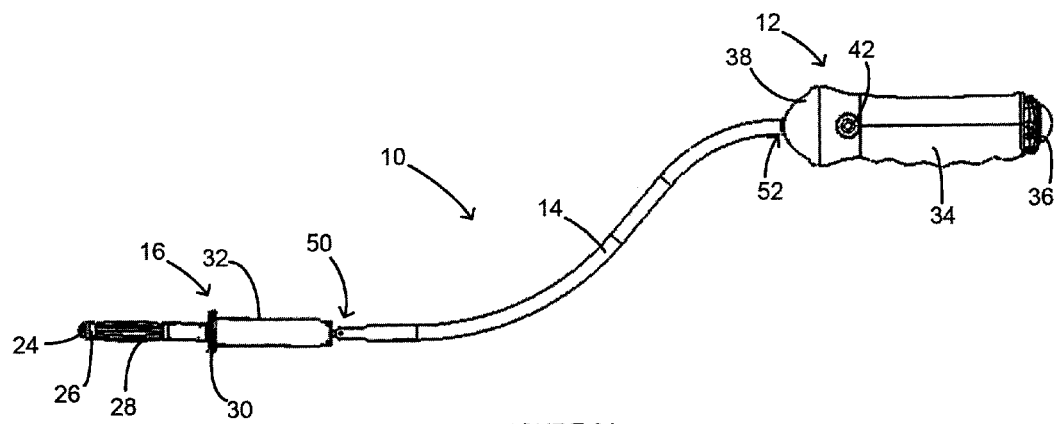
FIGS. 8A and 8B are side views of the uterine manipulator of FIG. 1 in a retracted position and an expanded position, respectively.
Figure 8B:
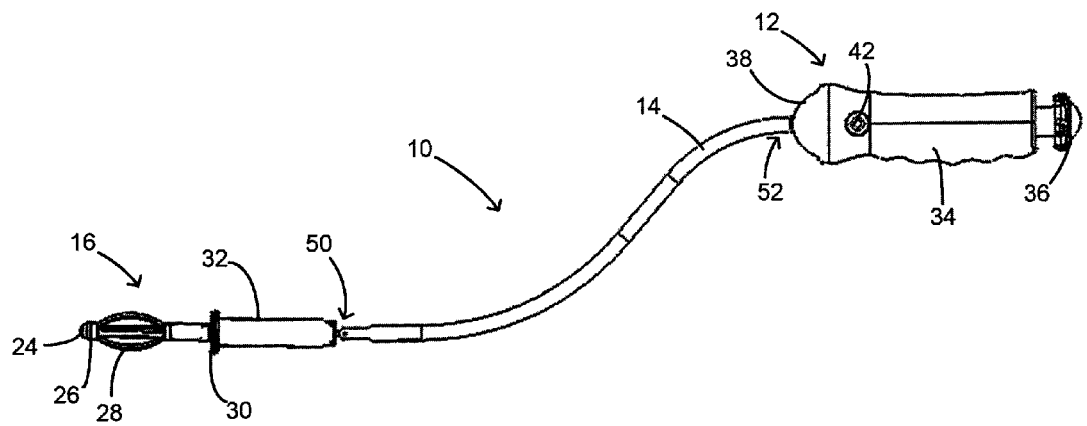
Figure 9A:
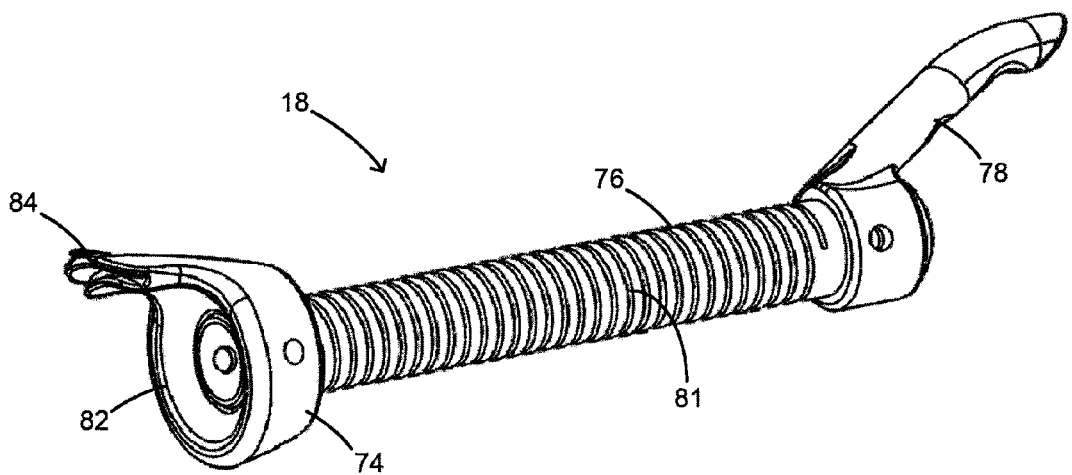
FIGS. 9A and 9B are perspective views of a cutting assembly and a backstop, respectively, of the uterine manipulator of FIG. 1.
Figure 9B:
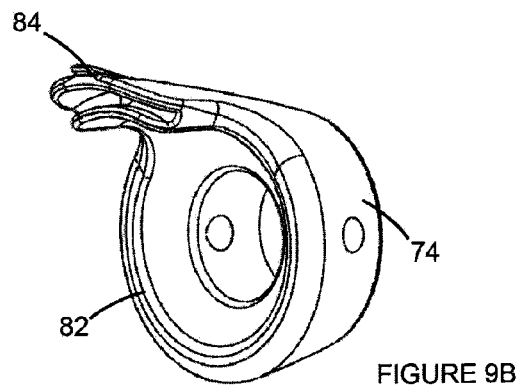

The tip assembly 16 can act as an umbrella-like expansion component capable of being adjusted between a retracted position and an expanded position. As a result, the tip assembly 16 can replace conventional intra-uterine balloon elements. The tip assembly 16 can be situated into the retracted position, as shown in FIGS. 8A and 12B, to facilitate insertion into the uterus 114 (e.g., until the abutment 30 reaches the cervix 112). Once inserted into the uterus 114, the tip assembly 16 can be deployed into the expanded position, as shown in FIGS. 8B and 12C, to facilitate a secure connection between the uterine manipulator 10 and the uterus 114 and cervix 112.

The expansion elements 28 can be spring-like elements capable of being in compression (e.g., shortened in length) and in tension (e.g., lengthened). Generally, pulling the expansion actuator 36 away from the handle housing 34 causes the expansion elements 28 to compress and expand outward circumferentially, situating the tip assembly 16 into the expanded position. Pushing the expansion actuator 36 back into the handle housing 34 causes the expansion elements 28 to retract back into tension and lengthen, situating the tip assembly 16 into the retracted position.

More specifically, when assembled, as shown in FIGS. 4B and 5B, the expansion tip 24 can slide into the tip shaft 26 until an end stop 64 of the expansion tip 24 reaches the end 66 of the tip shaft 26. The expansion elements 28 can fit over the tip shaft 26 until a first end 68 of the expansion elements 28 reaches the end 66 of the tip shaft 26. Both the expansion tip 24 and the tip shaft 26 can be slid into the tip housing 32, while the second end 70 of the expansion elements 28 can rest against an outer edge 72 of the tip housing 32. Pulling the expansion actuator 36 outward from the handle housing 34 causes the expansion connectors 48 to pull the expansion tip 24, and the tip shaft 26, further into the tip housing 32. Because the expansion elements 28 rest against the edge 72 of the tip housing 32, they are compressed (i.e., shortened in length) when the expansion tip 24 and the tip shaft 26 are forced into the tip housing 32. Shortening of the expansion elements 28 causes them to expand in their circumferential direction, therefore situating the tip assembly 16 into the expanded position. In the reverse, pressing the expansion actuator 36 back into the housing releases the pulling tension of the expansion connectors 48 on the expansion tip 24. The expansion elements 28 can be in a resting state when in tension and thus, without the pulling tension by the expansion connectors 48, the expansion elements 28 will revert back to their resting, retracted state, thereby pulling the expansion tip 24 and the tip shaft 26 back out from the tip housing 32 and situating the tip assembly 16 into the retracted position.

Figure 10A:
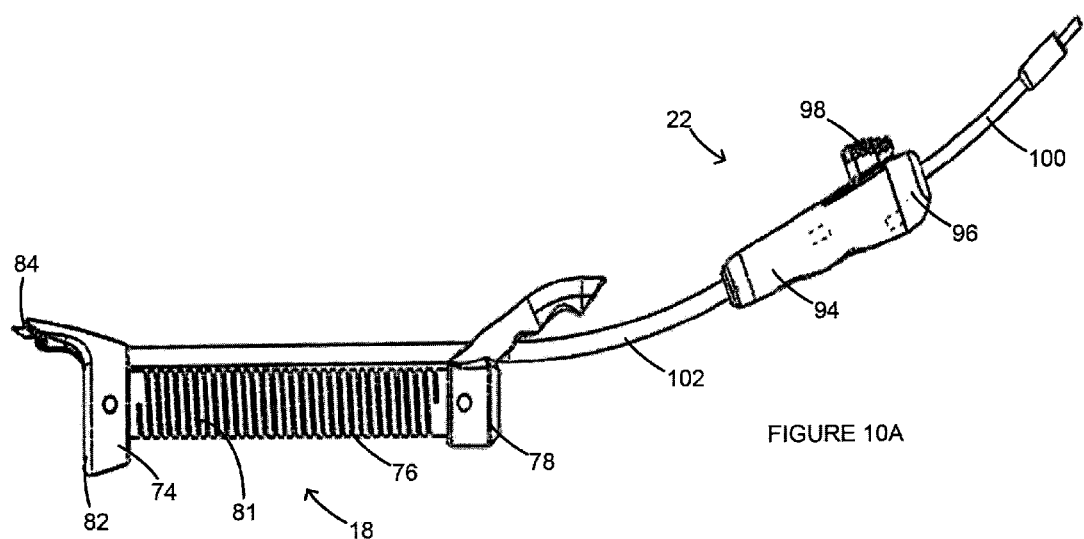
FIGS. 10A and 10B are side views of the cutting assembly and an electrical connector assembly, respectively, of the uterine manipulator of FIG. 1.
Figure 10B:
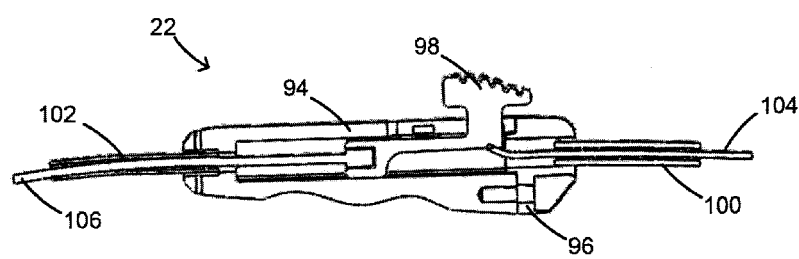
Figure 12D:
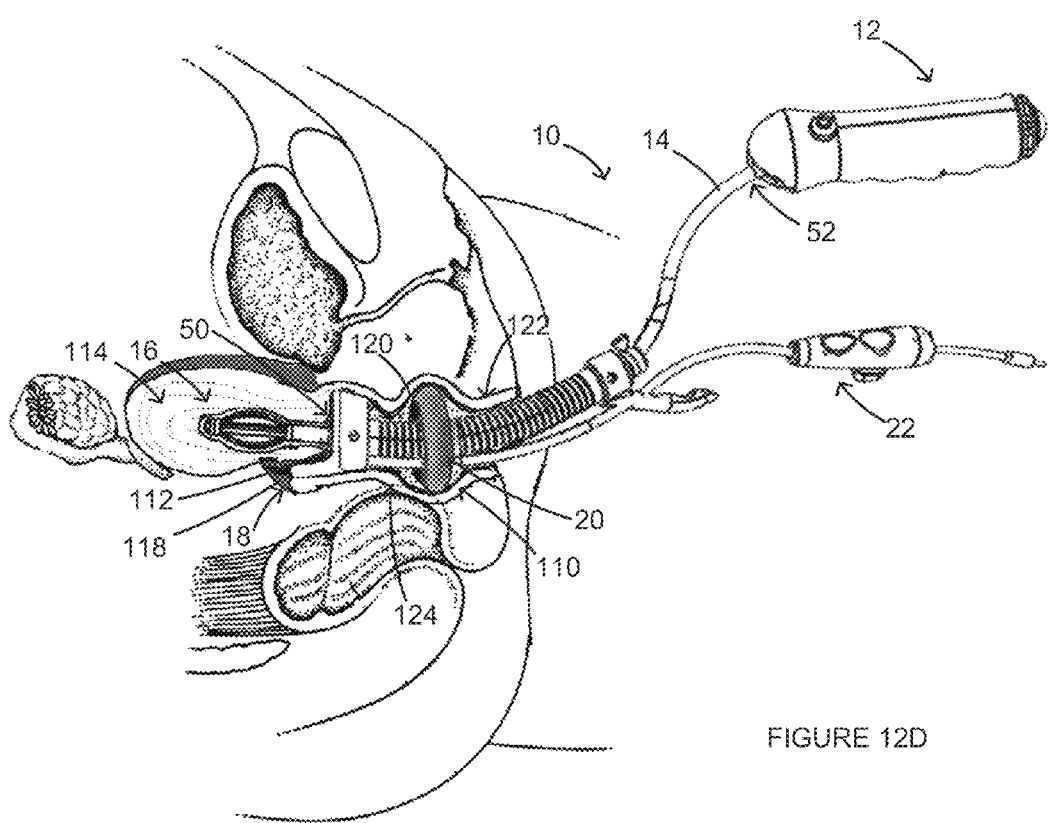

Referring back to FIGS. 1 and 2, the cutting assembly 18 can be slid over the shaft 14 and can be rotatable about the shaft 14. The cutting assembly 18 can include a backstop 74, a tube 76, a cutting handle 78, fasteners 80, and a spring 81. The backstop 74 can be positioned at a first end of the tube 76 and the cutting handle 78 can be positioned at a second, opposite end of the tube 76. The tube 76 can be slid over the shaft 14 and the cutting handle 78 can help maneuver the cutting assembly 18 along and/or around the shaft 14. The fasteners 80 can help fix the cutting assembly 18 in place along the shaft 14. The backstop 74 can receive the cervix 112 and come in contact with the vaginal fornix 118 when the uterine manipulator 10 is in position. The backstop can then be maneuvered in a circular manner to cut around the cervix 112 for detaching the cervix 112 and the uterus 114 from the vagina 110, as shown in FIG. 12D. More specifically, as shown in FIGS. 10A and 10B, the backstop 74 can include a round cup portion 82 and a cutter 84 extending outward from the cup portion 82. During use, the cutting assembly 18 can be pressed up against the abutment 30 of the tip assembly 16 so that the cup portion 82 extends past the abutment 30 and engages the fornix, stretching and forcing the fornix upward and away from the ureters. The cutter 84 can pierce through the tissue of the fornix, transecting the uterus 114 and the cervix 112 from the top of the vagina 110.

The cutting assembly 18 can be rotated about the shaft 14 (e.g., by the cutting handle 78), allowing the cutter 84 to travel in a circle at the junction of the cervix 112 and the vagina 110 and permitting complete transection of the uterus 114 and the cervix 112 from the vagina 110. The spring 81 can help distribute rotational forces evenly across the tube 76 when the cutting assembly 18 is rotated, for example, to prevent the tube 76 from breaking due to excess torque concentrated along one portion of the tube 76.

The electrical connector assembly 22 can advance the cutter 84 outward from the cup portion 82 to achieve the detachment procedure described above, and can retract the cutter 84 inward to facilitate insertion of the uterine manipulator 10 into the uterus 114 without piercing the vaginal walls 120 prior to proper positioning of the uterine manipulator 10. In addition, the electrical connector assembly 22 can provide an electrical connection between the cutter 84 and an electrosurgical unit (not shown) in order to provide hemostasis during the detachment procedure. The electrical connector assembly 22 can include a handle 94, a cap 96, a button 98, tubing 100, 102, and electrical connectors 104, 106. On one end of the electrical connector assembly 22 (i.e., adjacent to the cap 96), the tubing 100 and the electrical connectors 104 can be routed to the electrosurgical unit. On the other end of the electrical connector assembly 22, the tubing 102 and the electrical connectors 106 can be routed to the cutter 84. The electrical connectors 104, 106 can be electrically connected through the button 98 so that current can be routed from the electrosurgical unit to the cutter 84. Also, the electrical connectors 106 can be coupled to the cutter 84 and the button 98 so that pressing the button 98 forward and backward causes the cutter 84 to extend and retract, respectively.

Figure 11:
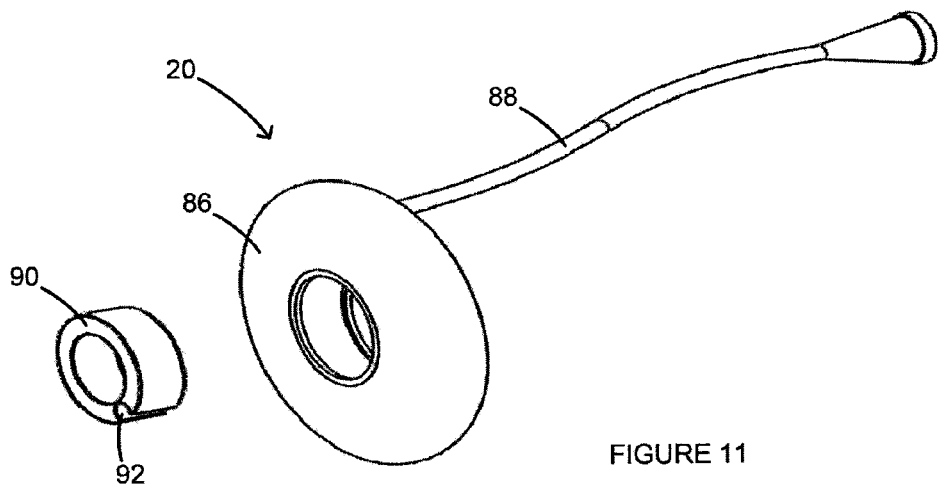
FIG. 11 is a perspective view of a pneumooccluder of the uterine manipulator of FIG. 1.

Referring to FIG. 11, the pneumooccluder 20 can include a balloon 86, a filling tube 88, and a bearing 90. The bearing 90 can be in contact with the tube 76 of the cutting assembly 18, and the balloon 86 can be positioned around the bearing 90. As shown in FIG. 11, the bearing 90 can include an outer groove 92 to allow passage of the electrical connector assembly tubing. During use, the pneumooccluder 20 can be positioned within the vagina 110 when the uterine manipulator 10 is set within the uterus 114. Once in position, the balloon 86 can be inflated via the filling tube 88 (e.g., with air, water, saline, or another fluid) in order to seal the distal vaginal cavity 122 from the proximal vaginal cavity 124. This can help maintain pneumoperitoneum once the incision has been made between the vagina 110 and the cervix 112 (i.e., causing the proximal vaginal cavity 124 to be in fluid communication with the abdominal cavity). As a result of the bearing 90, the shaft 14 and/or the cutting assembly tube 76 can be rotated without requiring rotation of the balloon 86. Because the balloon 86 can be set in place and does not need to be rotated when the shaft 14 or the cutting assembly 18 is rotated, the risk of losing pneumoperitoneum is greatly reduced.

Thus, the uterine manipulator 10 can be inserted into a patient's vagina 110 while in the retracted position, as shown in FIG. 12A. The uterine manipulator 10 can then be further guided through the vagina 110, past the cervix 112, and into the uterus 114, while still in the retracted position, as shown in FIG. 12B. Once set in the uterus 114, the uterine manipulator 10 can be situated into the expanded position, as shown in FIG. 12C, in order to facilitate a secure connection between the uterine manipulator 10 and the uterus 114. In addition, once the uterine manipulator 10 is set within the uterus 114, the pneumooccluder 20 can contact the vaginal wall 120 in order to seal the uterus 114 from the outside environment and the backstop 74 can abut the vaginal fornix 118, causing it to stretch upward. Once the uterine manipulator 10 is situated into the expanded position, the cutter 84 can be extended and the cutting handle 78 can be rotated in order to transect the uterus 114 and the cervix 112 from the top of the vagina 110. The uterine manipulator 10 of the present invention and its above-described procedures can thus eliminate the need for a colpotomy incision via laparoscopic tools, as is required in conventional laparoscopically assisted vaginal hysterectomies.

Embodiments of the invention may include any combination of one or more of the above-described components and/or other conventional uterine manipulator components. The above-described components, such as the cutting assembly 18, the tip assembly 16, and the pneumooccluder 20 can function independent from one another and therefore can be individually incorporated into a uterine manipulator with or without the other components. For example, it may be preferable to include the pneumooccluder 20 as described above with a conventional uterine manipulator to best execute a specific pelvic procedure.

Figure 13:
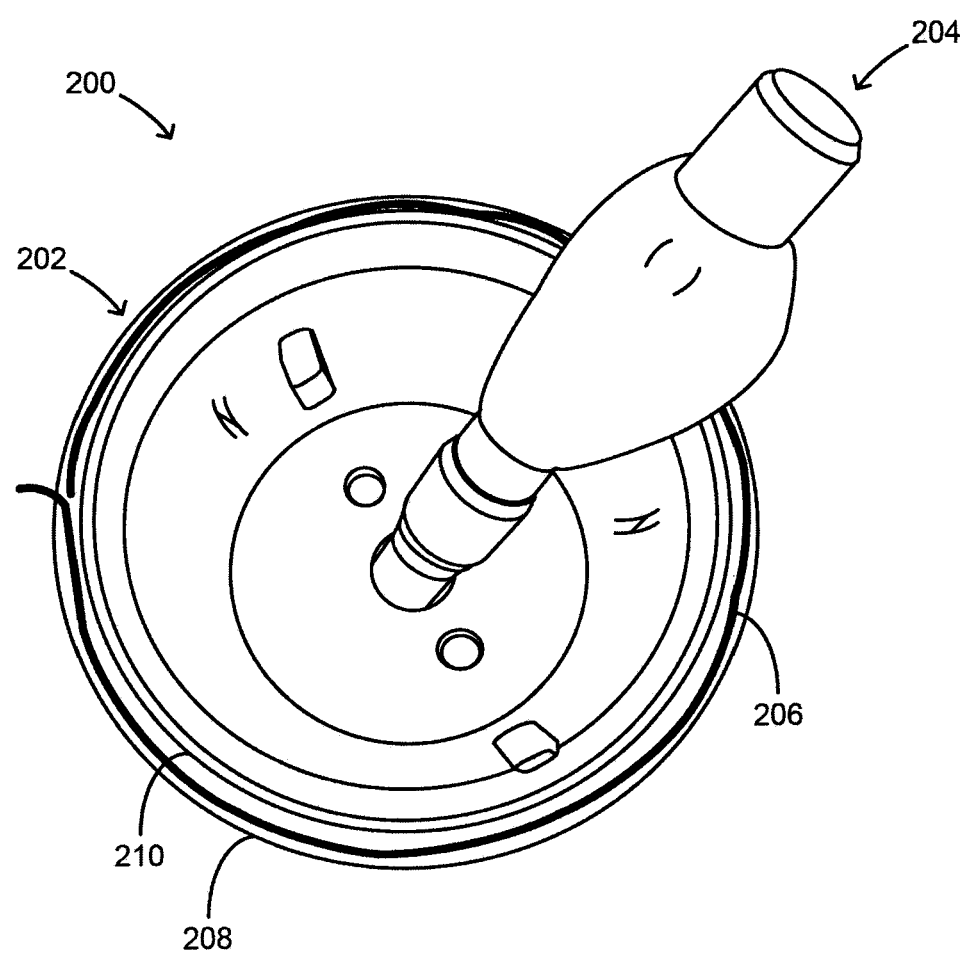
FIG. 13 is a perspective view of a manipulator, cup, and cutting assembly in accordance with the present invention.

For example, referring to FIG. 13, a cutting assembly 200 is illustrated. The cutting assembly 200 may be used with the functional uterine manipulator 10 of the preceding figures or may be used with other systems. The cutting assembly 200 includes a cup portion 202 and an expansion tip 204 extending therethrough. As illustrated, the expansion tip 204 may be a balloon-type design or other configurations, such as described above. Associated with the cup portion 202 is a cutter 206. The cup portion 202 is designed to engage the cervix, such as previously described. The cutter 206 is formed as a narrow wire embedded between two grooves 208, 210 on the cup portion 202.

Figure 14:
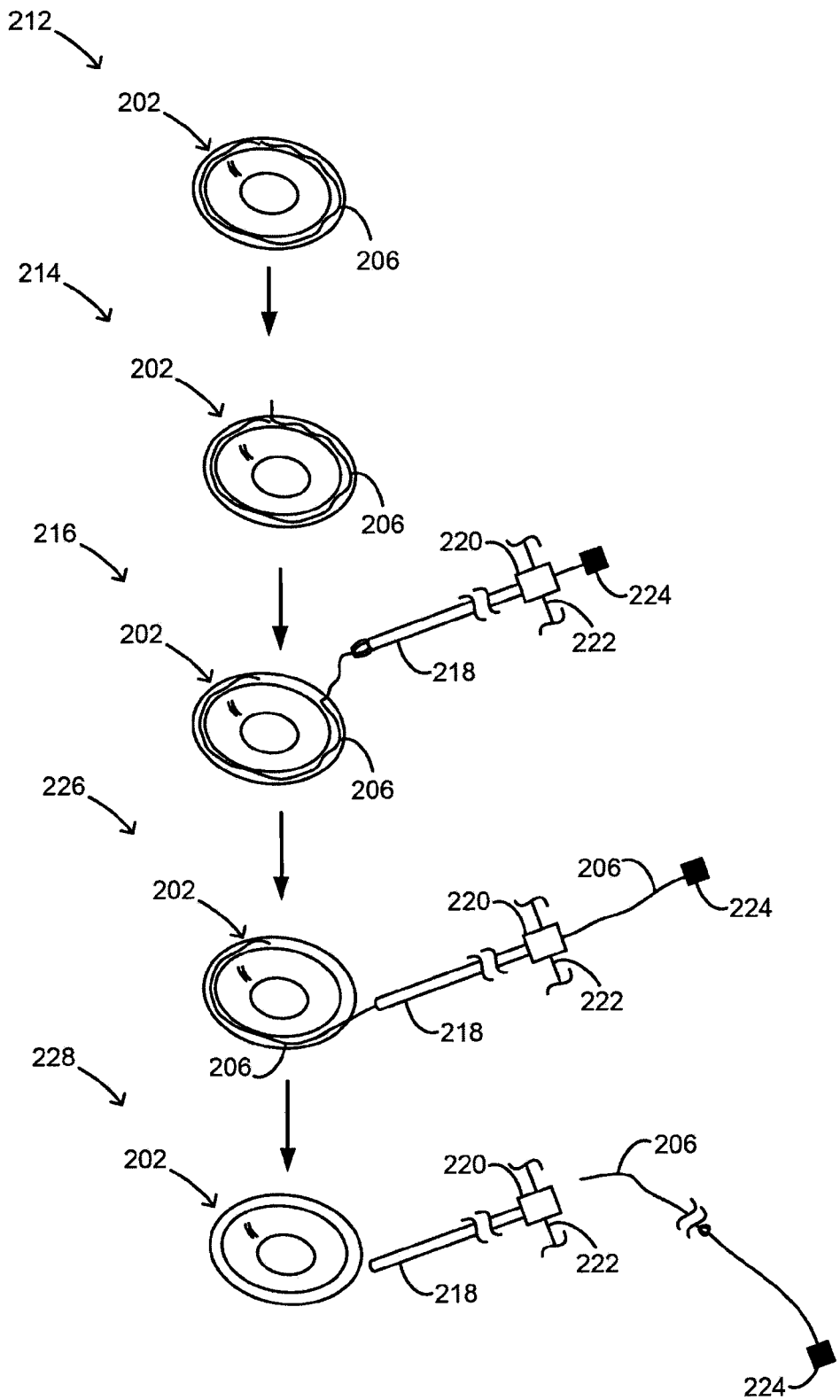
FIG. 14 is a series of views showing use of the cutting assembly of FIG. 13 in accordance with the present invention.

Referring to FIG. 14, the cutter 206 is designed to move from a stored position 212 to an extended position 214 where the cutter 206 may be pushed through the top of the vagina and, in a further extended position 216, pulled in by a laparoscopic instrument 218 that is introduced laparoscopically. The instrument 218 includes a trocar 220 that extends through the skin 222 to present a handle 224 to the clinician. Using the handle 224, the instrument 218 pulls the cutter 206 at position 226 and this, in turn, cuts the vagina and separates it from the cervix and uterus. The cutter 206 can either cut the vagina "cold" (without electrical current) or with an electrical current, based on surgeon preference. At a final position 228, the cutter 206 can be separated from the cup portion 202. The cutter 206 is generally covered by a laparoscopic instrument 218. That is the cutter 206 is pulled into the laparoscopic instrument 218, thereby enhancing safety given that the cutting wire or blade is not exposed at any given time.

In addition, the uterine manipulator 10 of the present invention, or at least one or more components of the uterine manipulator 10, can be used with orifice-assisted small incision surgeries (OASIS). In such surgeries, instrumentation may be inserted through a patient's belly button as well as the patient's vagina 110. This method decouples the optical axis (e.g., of a laparoscope inserted through the belly button) from the operative axis (e.g., of a surgical tool inserted through the vagina 110). In some implementations, the uterine manipulator 10 can include an extension tool to assist with OASIS procedures.

The present invention has been described in terms of one or more preferred embodiments, and it should be appreciated that many equivalents, alternatives, variations, and modifications, aside from those expressly stated, are possible and within the scope of the invention.

The invention claimed is:

1. A uterine manipulator adapted for insertion into a uterus, the uterine manipulator comprising:
   a shaft including a first end and a second end;
   a handle coupled to the first end;
   a tip assembly coupled to the second end and adapted for insertion into the uterus, the tip assembly including:
      a tip housing;
      a tip shaft retractable within the tip housing;
      an expansion tip retractable within the tip housing and including a substantially rounded tip covering a distal end of the tip shaft; and
      expansion elements positioned over the tip shaft and abutting an edge of the tip housing, the expansion elements extending from the distal end of the tip shaft to the edge of the tip housing, the tip assembly capable of being situated into an expanded position where the tip shaft is retracted into the tip housing, causing the expansion elements to expand outward in their circumferential direction, and a retracted position where the tip shaft is retracted out from the tip housing, causing the expansion elements to retract inward in their circumferential direction.

2. The uterine manipulator of claim 1 wherein the tip assembly is capable of being inserted into the uterus when situated in the retracted position and is capable of being stabilized within the uterus when situated in the expanded position.

3. The uterine manipulator of claim 1 further comprising an expansion actuator positioned on the handle and expansion connectors coupled between the expansion actuator and the expansion tip, wherein pulling the expansion actuator causes the tip assembly to be moved into the expanded position.

4. The uterine manipulator of claim 3 wherein the expansion elements are spring-like elements that are in tension when the tip assembly is situated in the retracted state and in compression when the tip assembly is situated in the expanded state, and wherein the expansion elements are in tension when at rest to allow the tip assembly to revert back to the retracted state when the expansion actuator is pressed back into the handle.

5. The uterine manipulator of claim 3 wherein the expansion connectors are routed from the expansion actuator, through the shaft, to the expansion tip.

6. The uterine manipulator of claim 1 further comprising connectors that couple the handle to the tip assembly.

7. The uterine manipulator of claim 1 wherein the handle is coupled to the first end in a pivotable manner and the tip assembly is coupled to the second end in a pivotable manner.

8. The uterine manipulator of claim 1 wherein the shaft is constructed of a non-rigid, flexible material.

9. The uterine manipulator of claim 1 and further comprising a cutter assembly coupled around the shaft and adapted to receive the cervix when the tip assembly is inserted into the uterus, the cutter assembly including a tube with a first tube end and a second tube end; a backstop coupled to the first tube end and including a cup portion and a cutter; and a cutting handle coupled to the second tube end.

10. The uterine manipulator of claim 1 further comprising a pneumooccluder coupled around the shaft and capable of being positioned within a vaginal cavity when the tip assembly is inserted into the uterus, the pneumooccluder including a bearing positioned around the shaft; a balloon positioned around the bearing; and an occluder tube coupled to the balloon; wherein the bearing is configured to allow the shaft to be rotated independently from the balloon.

11. The uterine manipulator of claim 1, wherein the handle is pivotable relative to the first end about a first axis; and the tip assembly is pivotable relative to the second end along a second axis parallel to the first axis.

12. The uterine manipulator of claim 11, wherein the tip assembly pivots in a first direction along a plane in response to the handle pivoting in a second, opposite direction along the plane.

13. The uterine manipulator of claim 11, wherein the tip assembly pivots above the second end and below the second end; and the handle pivots above the first end and below the first end.

14. The uterine manipulator of claim 11, wherein the tip assembly is pivotable about the first axis in a range of degrees to enable both raising and lowering the uterus.

15. The uterine manipulator of claim 14, wherein the handle includes a curved track, and a hinge pin slidable within the track for the range of degrees.

\* \* \* \* \*